(12) United States Patent
Russell et al.

(10) Patent No.: US 6,838,057 B2
(45) Date of Patent: Jan. 4, 2005

(54) POWER DISRUPTION APPARATUS FOR A RADIATION LAMP

(75) Inventors: Scott P. Russell, Rutland, VT (US); James R. DiSabito, Brandon, VT (US); Mark E. Kurtz, Ft. Lauderdale, FL (US)

(73) Assignee: Ultravation, Inc., Brandon, VT (US)

( * ) Notice: Subject to any disclaimer, the term of this patent is extended or adjusted under 35 U.S.C. 154(b) by 0 days.

(21) Appl. No.: 10/476,600

(22) PCT Filed: May 7, 2002

(86) PCT No.: PCT/US02/14433
§ 371 (c)(1),
(2), (4) Date: Oct. 31, 2003

(87) PCT Pub. No.: WO02/089859
PCT Pub. Date: Nov. 14, 2002

(65) Prior Publication Data
US 2004/0161371 A1 Aug. 19, 2004

Related U.S. Application Data
(60) Provisional application No. 60/289,345, filed on May 7, 2001.

(51) Int. Cl.[7] ............................. A62B 7/08; G01N 23/00
(52) U.S. Cl. .................. 422/121; 422/120; 250/455.11; 250/461.1
(58) Field of Search .......................... 422/121, 120, 422/24, 20, 22; 250/455.11, 461.1, 432 R; 315/56–58

(56) References Cited
U.S. PATENT DOCUMENTS

| | | | |
|---|---|---|---|
| 2,472,977 A | 6/1949 | Mageoch et al. ........... 172/328 |
| 4,799,896 A | 1/1989 | Gaynor et al. .............. 439/232 |
| 5,422,487 A | * 6/1995 | Sauska et al. .............. 250/436 |
| 5,742,063 A | 4/1998 | Scroggins et al. ...... 250/455.11 |
| 5,753,996 A | 5/1998 | Csoknyai ............... 313/318.05 |
| 5,866,076 A | 2/1999 | Fencl et al. ................. 422/121 |
| 5,902,552 A | 5/1999 | Brickley ..................... 422/121 |
| 5,968,455 A | 10/1999 | Brickley ..................... 422/121 |
| 6,039,460 A | * 3/2000 | Ng et al. .................... 362/267 |

* cited by examiner

Primary Examiner—Tuyet Thi Vo
(74) Attorney, Agent, or Firm—Law Offices of Kenneth F. Dusan

(57) ABSTRACT

Radiation module (10) comprises a power disruption apparatus (11) for a radiation lamp (14) to disinfect a fluid passing through a conduit (12). Radiation lamp (14) includes lamp base (15) that supports lamp tubing (14a) at one end thereof, terminal pins (17,17a) and flange (28) disposed about lamp base (15). Power disruption apparatus (11) includes mounting plate (16) provided with opening (27) for registry with opening (25) in duct (12). Openings (25,27) are sized to receive lamp tubing (14a) therethrough. Flange (28) interfaces with mounting plate (16) to restrict axial movement of lamp base (15) into duct (12). Module (10) also includes compression nut (22) for detachably securing lamp base (15) to mounting plate (16), and electrical socket (20) for receiving terminal pins (17,17a). Electrical socket (20) is detachably mounted to compression nut (22) in a manner that prevents detachment of compression nut (22) from mounting plate (16) for the removal of radiation lamp (14) from duct (12) without prior detachment of electrical socket (20) from electrical pins (17,17a).

36 Claims, 13 Drawing Sheets

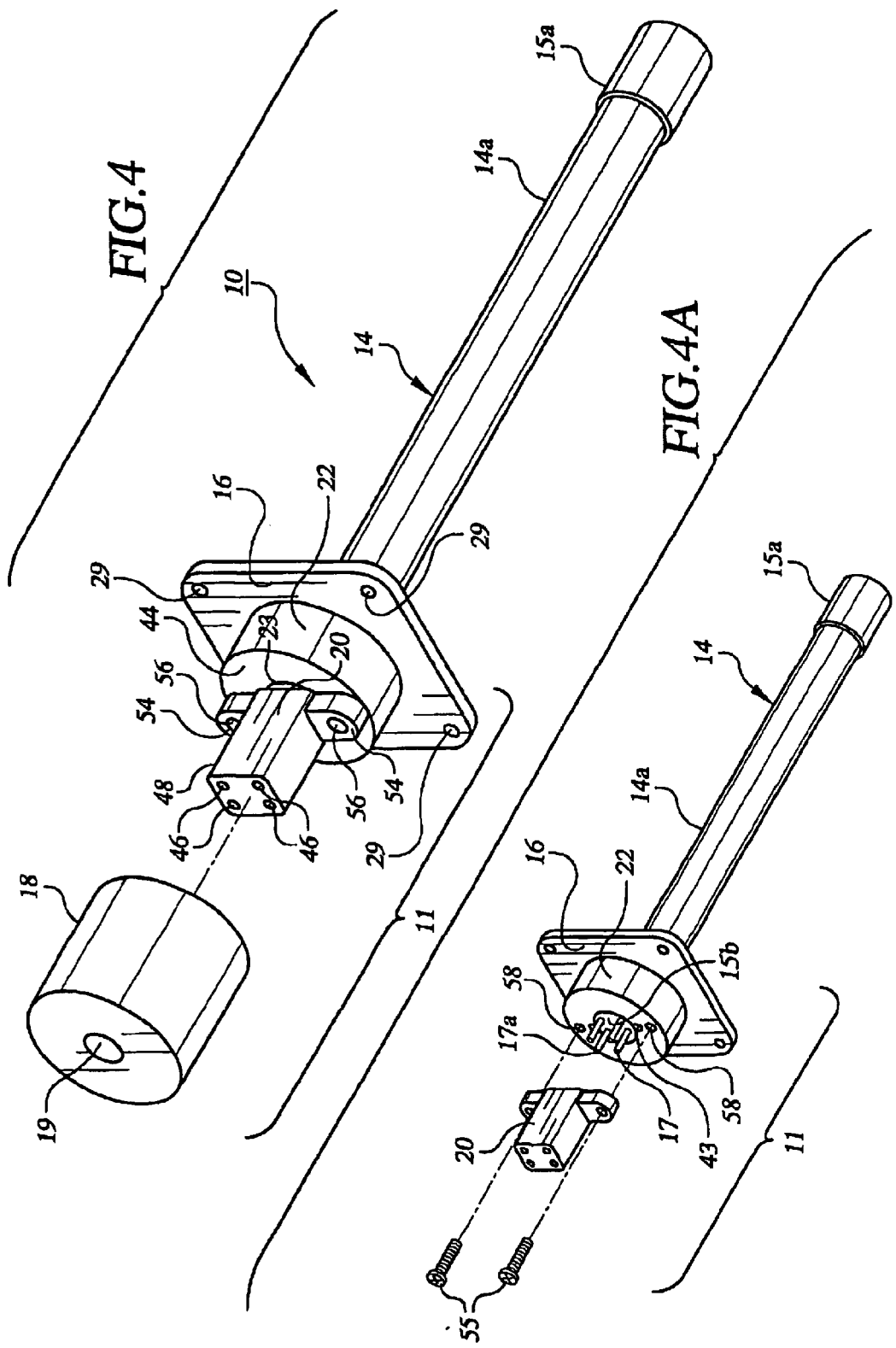

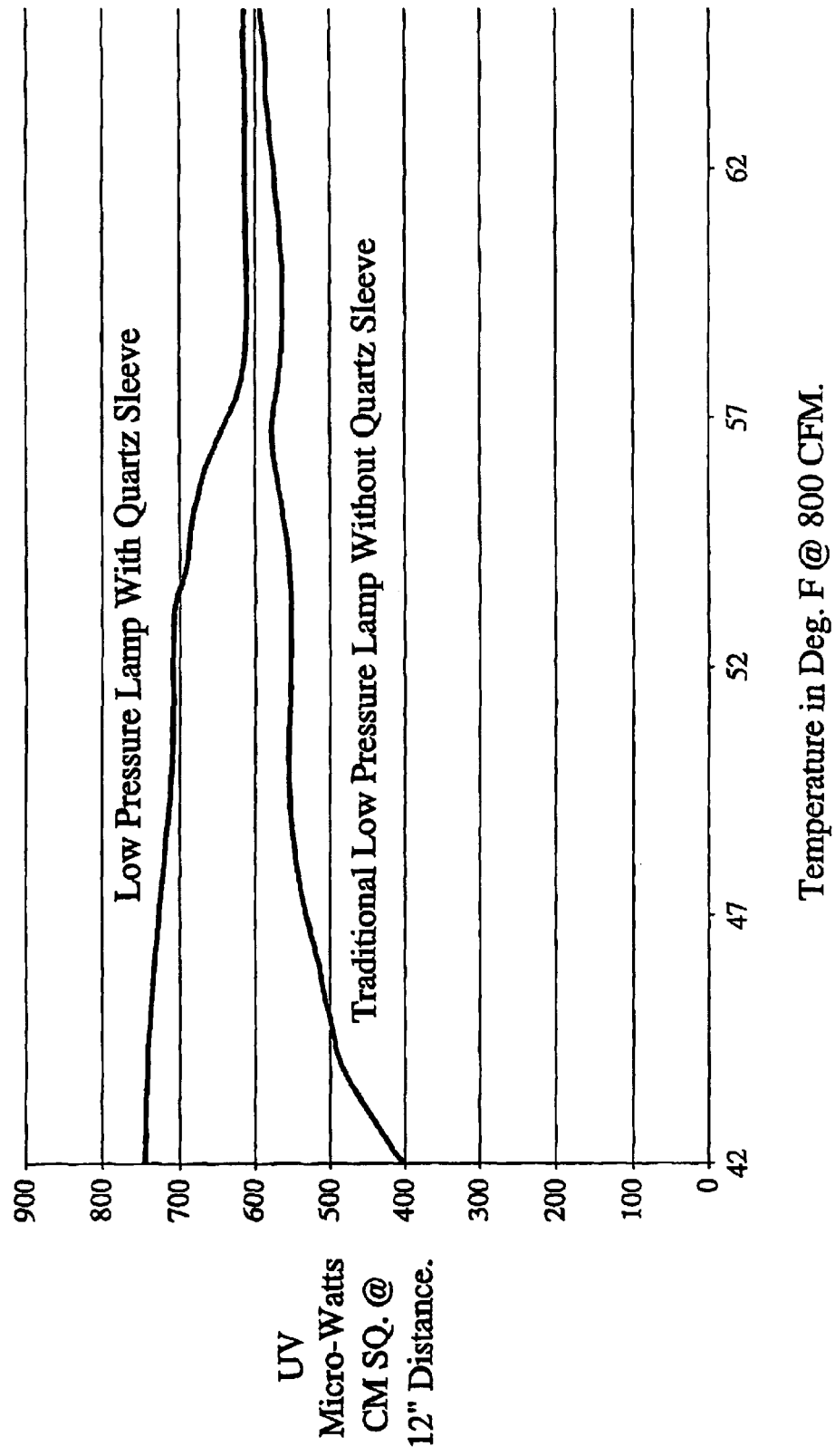

POWER DISRUPTION APPARATUS FOR A RADIATION LAMP

This application claims priority to U.S. Provisional Patent Application Ser. No. 60/289,345 filed 07 May 2001.

BACKGROUND OF THE INVENTION

1. Field of the Invention

This invention relates to an improvement in an air disinfection apparatus, and more particularly to an improved apparatus for the disruption of power to a source of radiation, typically a radiation lamp that generates ultraviolet light, when the active radiation source is removed from a confined space, for example, a HVAC ("heating/ventilation air conditioning") duct. The invention further relates to an air disinfection module that incorporates such an apparatus within a HVAC, and a method for guaranteeing disruption of power to a radiation source when the active radiation source is removed from a confined space.

2. Related Art

Germicidal lamps that generate ultraviolet light are now being used in HVAC duct systems for the disinfection of bacteria transported with the air. The germicidal or ultraviolet (hereinafter "UV") lamps employed in HVAC ducts are generally powered by a source of electricity commonly located externally of the duct. The removal of the lamp(s) from the HVAC duct, however, presents a safety problem in that the UV lamp's power may not be discontinued during its removal, e.g., by disconnecting a plug from a wall socket or by disconnecting the lamp's electrical connection with a ballast. The prolonged exposure to the ultraviolet radiation emitted from the lamp, along with the lamp's intensity, may cause serious injury to the eyes or touch if precautions are not taken to shut the lamp down before its handling or removal from the HVAC duct. In addition, the efficiency for generating ultraviolet light by a UV radiation lamp varies widely depending on the operating environment that the lamp is subject to, e.g., the temperature variations in a HVAC duct due to the cooling of the air passing through the duct during the warmer months of the year, and heated duct air during the winter months. It therefore becomes desirable to provide a safety mechanism that assures the disconnection of a radiation lamp before its removal from a duct. It is also desirable to maintain an operating environment for the lamp that will enable it to perform at peak efficiency with maximum longevity.

An apparatus for sterilizing air using ultraviolet radiation emitting probes inserted into an air duct is generally described in U.S. Pat. No. 5,742,063 issued to Scroggins et al. on 21 Apr. 1998. Various lamp socket configurations have also been disclosed in the prior art. For example, FIGS. 5 and 6 of U.S. Pat. No. 2,472,977 issued to Mageoch et al. on 14 Jun. 1949, disclose a fluorescent lamp socket formed of a body member 13 that has a cylindrical recess 18 and a collar 29 that fits over an opening 35 within a supporting panel 36 of a fluorescent light fixture. The body member 13 has external mounting flanges 15 for mounting to collar 29 and panel 36. In order to insure proper registry of body member 13 and collar 29, the collar is provided with an axially extending cup-shaped projection 31 adapted to nest in the annular seat 17 of the cylindrical recess 18 of body member 13. The body member 13 and collar 29 are permanently secured to the supporting panel 36 by rivets 32.

FIG. 6 of U.S. Pat. No. 5,902,552 issued to Brickley on 11 May 1999, illustrates an ultraviolet air sterilization device 10 containing a housing unit 12 and one or more internally threaded conduit mounting flanges 16 connected to germicidal lamps that protrude into the air stream of an air handling duct 11. Receptacles 30 are constructed of a UL approved plastic material with external threads 32 for engagement with mounting flanges 16. Each receptacle has an opening 34 for receiving a transfer cable 50 containing wires 53 which are connected to pins 26 on base 22 of lighting element 24. A grounded power supply plug 40 with cord 42 is used to provide power to the sterilization device 10 via a ballast. Power is transferred from the ballast through transfer cables 46 to transfer cables 50 of the receptacle 30. FIG. 6 of U.S. Pat. No. 5,968,455 issued to Brickley on 19 Oct. 1999 illustrates a similar arrangement.

U.S. Pat. No. 5,866,076 issued to Fencl et al. on 2 Feb. 1999, discloses an ultraviolet lamp comprising a tube and a fixture for supporting the tube at one end only, the fixture being mounted on the inside or outside of a single wall of a HVAC duct. As shown in FIG. 3, the fixture has a stem 135 into which the tube is inserted and a ring 131 about the stem. A mounting mechanism in the form of a spring clamp 510 is biased against the ring 131 for holding the stem 135 in place. A gasket 400 is interposed between the ring 131 and wall 210 of fixture 200 to act as a shock absorber and vibration damper.

Disclosures of more complex sockets for "twin tube" fluorescent lamps sharing a common base are contained in U.S. Pat. No. 4,799,896 issued to Gaynor et al. on 24 Jan. 1989.

SUMMARY OF THE INVENTION

In accordance with a broad aspect of the invention, an air disinfection assembly is provided comprising a radiation module for incorporation with a conduit containing the passage of a fluid, typically air, therethrough. The module comprises a radiation lamp for generating ultraviolet light that includes a lamp base which supports (i) at least one lamp tubing at one end thereof, (ii) a plurality of axially extending terminal pins, typically four, and (iii) a retention member. The retention member is typically a flange that is disposed about at least a portion of the circumference of the lamp base.

In addition to the radiation lamp, the module additionally comprises a power disruption apparatus that includes a mounting member, preferably having a flat plate-like construction, provided with an opening that receives the lamp tubing of the radiation lamp therethrough. The opening in the mounting member is configured in size to enable the retention member of the lamp base to restrict its axial movement beyond the mounting member. This prevents the radiation lamp from falling into the interior of a conduit, such as an HVAC duct, when the power disruption apparatus is mounted to the conduit, typically with a fastening means such as screws, threaded bolts, etc.

A coupling member is also provided which is mounted to the mounting member for detachably securing the lamp base to the mounting member. The coupling member preferably comprises an annular collar whose annular opening is configured for receiving therein the lamp base that supports the terminal pins. The annular collar is also provided with fastening means, e.g., screws, threaded bolts, or any other conventional attachment means, for detachably securing the collar to the mounting member about the lamp base. This arrangement allows the mounting member and radiation lamp to be incorporated with the conduit, the latter having its lamp tubing extending into the interior of the conduit in a direction that is usually transverse to the flow of fluid passing therethrough.

The power disruption apparatus also includes an electrical coupling member, e.g., an electrical socket that includes electrical receptacles, for receiving the terminal pins of the lamp base. The electrical coupling member is configured to detachably mount to the coupling member in a manner that prevents detachment of the collar member from the mounting member without the prior decoupling of the electrical coupling member from the electrical terminal pins of the lamp base. In one embodiment, the electrical coupling means may be configured in the form of a female electrical socket that not only connects with and receives the terminal pins of the lamp base, but also obstructs access to the fastening means which detachably secures the coupling member to the mounting member. In this manner, withdrawal of the radiation lamp from the conduit interior or removal of the coupling member from the mounting member can only be undertaken if the electrical coupling member, e.g., the electrical socket, is disconnected from the radiation lamp. This has the effect of disrupting total electrical power to the lamp and avoids the harmful effects of exposure to the radiation generated by the lamp when it is powered. In another embodiment, the electrical socket may also include an obstruction member that obstructs access to the fastening means of the annular collar when the socket is connected to the terminal pins of the radiation lamp. The obstruction member may take the form of extension members laterally extending from the socket which obstruct access to the fastening means of the annular collar member when the socket is electrically engaged with the terminal pins of the radiation lamp. In yet another embodiment of the invention, the obstruction member may take the form of an annular obstruction member disposed between the socket and the annular collar for preventing access to the fastening means of the annular collar.

The retention member, mounting member and collar member elements described above may be integrated into a unitary structure by disposing a mounting member about the end of the lamp base which supports the terminal pins. The mounting member is sized for detachable securement to the conduit with a fastening means, such as one or more threaded fasteners, which has the effect of restricting the axial movement of the lamp base into the interior of the conduit. As a preference, the mounting member is integral with the lamp base. The electrical coupling member is detachably mounted to this mounting member for electrical engagement with the terminal pins of the lamp base in a manner that prevents detachment of the mounting member from the conduit without prior detachment of the electrical coupling member from the terminal pins of the radiation lamp. As with the power disruption apparatus described above, the electrical coupling member preferably comprises an electrical socket that includes electrical receptacles for receiving the terminal pins of the lamp base, and is configured to obstruct access to the fastening means of the mounting member when the electrical socket is mounted to said mounting member. The radiation module may optionally include a radiation pervious protective sleeve which is configured to encompass the radiation lamp. The protective sleeve is closed at one end and open at the opposite end for slidable mounting to the radiation lamp. The open end of the protective sleeve, which is preferably constructed of fused quartz, is secured about the lamp base of the radiation lamp, directly to the mounting member itself, or both.

In accordance with another aspect of the invention, the radiation lamp may also embody a lamp base that supports two or more lamp tubings at one end thereof. The lamp base, which is common to one end of the plurality of lamp tubings, includes a plurality of axially extending terminal pins, preferably two or four. In addition to the multiple tube radiation lamp, the radiation module also includes (i) a mounting member provided with an opening for receiving the lamp tubings therethrough; (ii) a retention member, preferably a flange means, for restricting the axial passage of the lamp base through the opening of the mounting member; (iii) a locking member disposed about the opening for detachably securing the lamp base to the mounting member, preferably one or more resilient clasps for detachable engagement with the lamp base; (iv) an electrical coupling member, e.g., an electrical socket, for electrical engagement with the terminal pins; and optionally, (v) electric transmission means connected to the electrical coupling member and at least one ballast for powering the radiation lamp. The electrical coupling member, e.g., an electrical socket that includes receptacles for receiving the terminal pins axially extending from the lamp base, is detachably secured to the mounting member in a manner that prevents detachment therefrom without prior disengagement of the electrical coupling member from the terminal pins of the lamp base.

The electrical socket preferably comprises an obstruction member that detachably mounts to the mounting member about the locking member in a way that prevents access to the locking member. The obstruction member may be configured as an extension disposed about at least a portion of the perimeter of the electrical socket. In this embodiment, the extension is provided with fastening means that detachably secures the electrical socket to the mounting member. More specifically, the extension may take the form of a lip disposed about the perimeter of the electrical socket. The lip is preferably configured to interface with the mounting member about the locking member, and is provided with at least one opening to accommodate the insertion of the fastening means for the detachable securement of the electrical socket to the mounting member.

The power disruption apparatus and/or radiation modules according to the invention may optionally include electric transmission means, e.g. cabling or wiring, connected to the electrical coupling member and to at least one ballast for powering the radiation lamp.

BRIEF DESCRIPTION OF THE DRAWINGS

A complete understanding of the present invention may be obtained by reference to the following specification when taken in conjunction with the accompanying drawings wherein certain preferred embodiments are illustrated and wherein like numerals refer to like parts throughout.

FIG. 4 is a left front isometric view of the assembled radiation module 10 shown in FIG. 2 with boot 18 separated from the top of the module.

FIG. 4A is a isometric view of the radiation module 10 illustrated in FIG. 4 with the boot removed and the electrical coupling member 20 exploded from the remainder of the module to expose the mounting plate 16 of the module.

FIG. 12A is an isolated isometric view of the electrical coupling 70 illustrated in FIG. 12.

FIG. 13A is a reverse isometric view of the socket 118 illustrated in FIG. 13.

FIG. 19 is a graph showing a comparison of the ultraviolet light output of a low pressure medium lamp over an operating temperature range, with and without the inclusion of a protective quartz sleeve.

DETAILED DESCRIPTION OF THE INVENTION AND PREFERRED EMBODIMENTS THEREOF

Throughout the following description, the preferred embodiments and examples are intended as exemplars rather than limitations on the apparatus, module and/or methods of the invention described below.

The present invention provides an improved apparatus and method for the disruption of power to a radiation source, e.g., a germicidal lamp such as an ultraviolet [hereinafter "UV"] lamp, when the radiation source is removed from a confined space or passageway, or designated area of operation, e.g., an HVAC duct or conduit. Such an apparatus and method assures the disruption of power to the UV lamp when the lamp is removed from its HVAC duct thereby avoiding exposure to the lamp's harmful radiation effects while the lamp is in operation. In accordance with the invention, a radiation module is provided that comprises a radiation source coupled with an apparatus for the disruption of power to the radiation source upon the radiation source's removal from its designated vicinity of operation.

Figure 1:
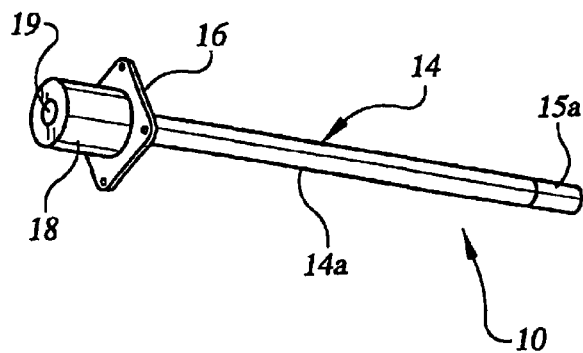
FIG. 1 is an isometric view of an assembled radiation module 10 in accordance with one aspect of the invention herein.
Figure 3:
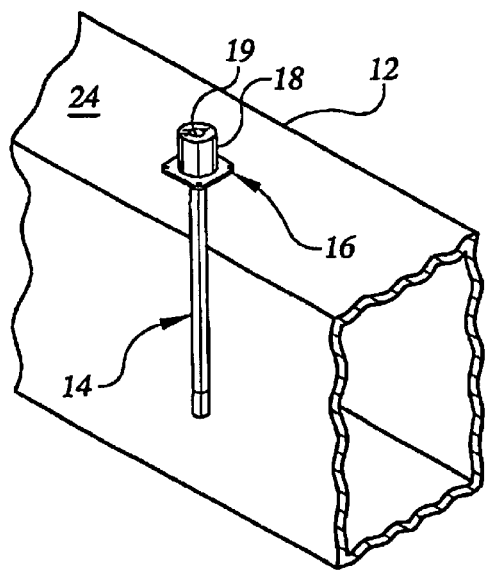
FIG. 3 is an isometric view of radiation module 10 in FIG. 1 mounted to a heating ventilation air-conditioning duct 12 illustrating the insertion of radiation lamp 14 into duct 12.

Referring to FIG. 1, a radiation module 10 for the treatment of air passing through a confined space, such as HVAC duct 12, is illustrated wherein, in one embodiment of the invention, radiation module 10 comprises a radiation source such as UV lamp 14, a mounting means in the form of, for example, mounting plate 16, a lamp fastening means, e.g., a coupling member in the form of compression nut 22, and an electrical receptacle means such as an electrical coupling member in the form of socket 20. A protective covering means, e.g., a dielectric boot 18 made of, for example, rubber (see FIG. 2), may optionally be added to the module, in which case boot 18 has an opening 19 in the top central covering portion thereof to facilitate the passage of an optional electrical conductor, e.g., electrical transmission cable 21, from socket 20 to an electrical power supply, e.g., a ballast 23 (see FIG. 10), which in turn is connected to a source of power external of module 10 via electrical plug 53.

Figure 7:
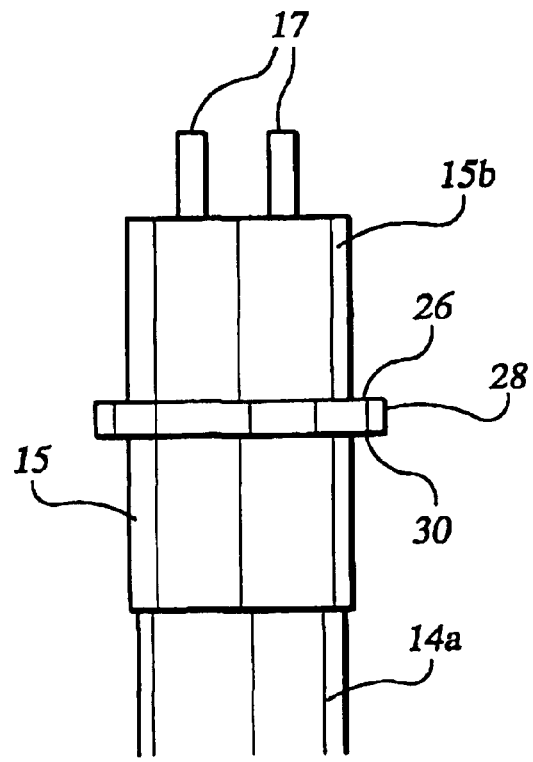
FIG. 7 is an elevated plan view of the top section of radiation lamp 14 illustrated in FIG. 6.
Figure 6:
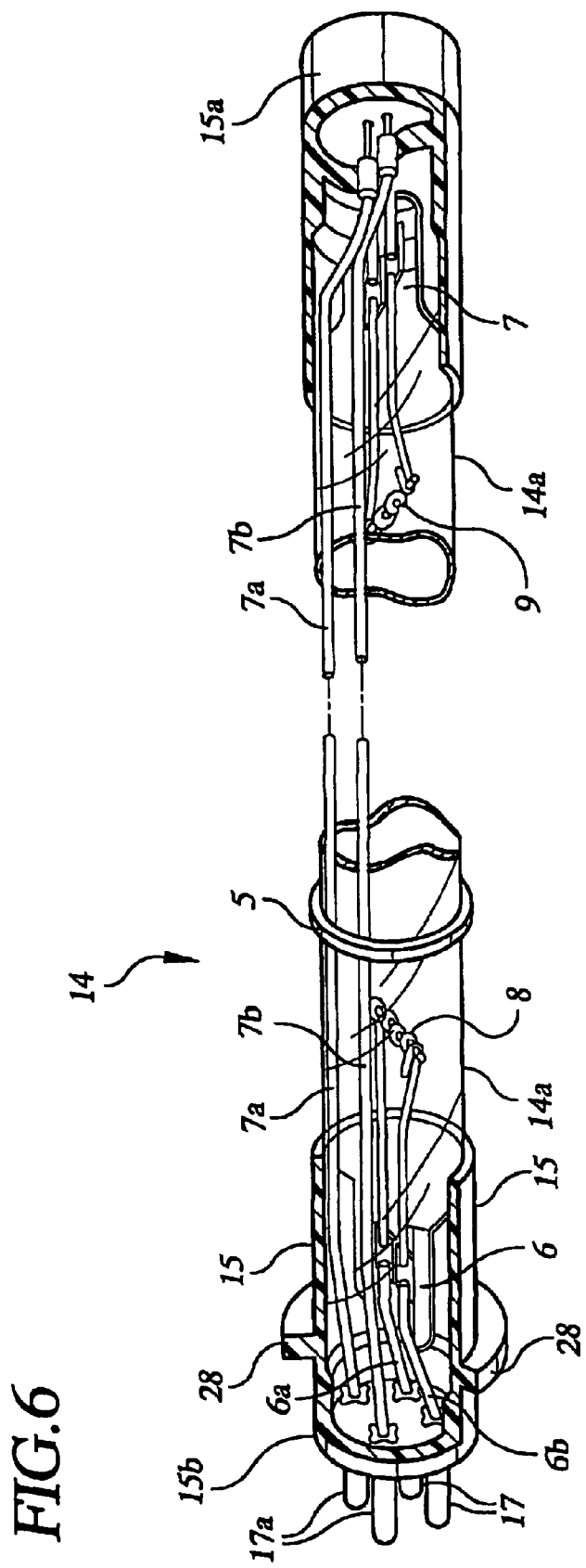
FIG. 6 is a detailed segmented isometric view of the radiation lamp 14 illustrated in FIGS. 1–5 and 7.

As best illustrated in FIGS. 6 and 7, UV lamp 14 is in the form of a fluorescent type lamp capable of emitting ultraviolet light at a wavelength that includes 254 nanometers, although it may also include 187 nanometers, the latter resulting in the creation of ozone. The UV lamp illustrated in greater detail in FIG. 6 is a conventional 4-pin lamp whose terminal pins 17,17a are supported at one end by lamp base 15. UV lamp 14 includes an elongate quartz tubing 14a supported at each end by lamp bases 15 and 15a. Quartz tubing 14a is sealed at both ends 6 and 7 which contain respective electrodes 8 and 9. The ends of electrode 6 are electrically coupled via appropriate conductor wires 6a,6b with a pair of terminal pins 17a, respectively, axially extending from lamp base 15. The ends of the opposite electrode 7 are electrically coupled with conductor wires 7a,7b which extend exteriorly of quartz tubing 14a and are connected to a pair of terminal pins 17 also axially extending from lamp base 15. A retaining ring 5 constructed of Teflon® is disposed about the mid section of quartz tubing 14a to contain conductor wires 7a,7b along the length thereof. While the lamp illustrated in the figured drawings is a quartz ("hard glass") four-pin UV lamp adapted for electrical connection to a power source, it will be appreciated that other types of terminal pins, numbers of terminal pins, e.g., two or more pins disposed at one end of the lamp, plugs and/or electrical connectors may be employed with the UV lamp that are adaptable for coupling directly or indirectly to a power source. As an example, in place of a "hard glass" lamp, a two- or four-pin "soft glass" UV lamp manufactured by the Phillips Corporation may be used which has a tubing that is permeable to ultraviolet light in the wavelength range that includes 254 nanometers.

The lamps commonly used in radiation module 10 are those that provide light transmission anywhere within the ultraviolet spectrum of light, i.e., within a light transmission range of approximately 150 to 400 nanometers. Ultraviolet lamps typically used are low pressure mercury lamps, although any lamp producing an ultraviolet light sufficient to have a destructive effect on germicidal activity, can be utilized. For example, high output, low pressure lamps may be used for the treatment of air in the HVAC duct. These lamps generally contain a thicker lamp filament in the lamp's electrodes to absorb higher current settings for the lamp's operation. If the lamp is able to operate at an increased temperature range, the deleterious effects of cooling air in the HVAC duct is avoided. Normally, as cooling air moves past the outside surface of the lamp tubing, the operating temperature of the lamp will be lowered thereby leading to a drop in the lamp's mercury pressure. As the mercury vapor pressure is lowered, ultraviolet output activity of the lamp can be significantly reduced which may also lead to premature aging of the lamp.

Lamps commonly known as "splice lamps" may also be used. These lamps, which can be high output/low pressure or low pressure lamps, comprise two different types of glass tubing, e.g., a first and second glass tubing, typically fused together end to end in the axial direction of the lamp. When the lamp is activated, the first glass tubing will generate ultraviolet light in the radiation wavelength range that will produce ozone, e.g., a range that includes a radiation wavelength of 185 nanometers and 254 nanometers. A second glass tubing of the "splice lamp" will generate ultraviolet light in a radiation wavelength range that includes 254 nanometers without the generation of any substantial amounts of ozone.

Figure 13:
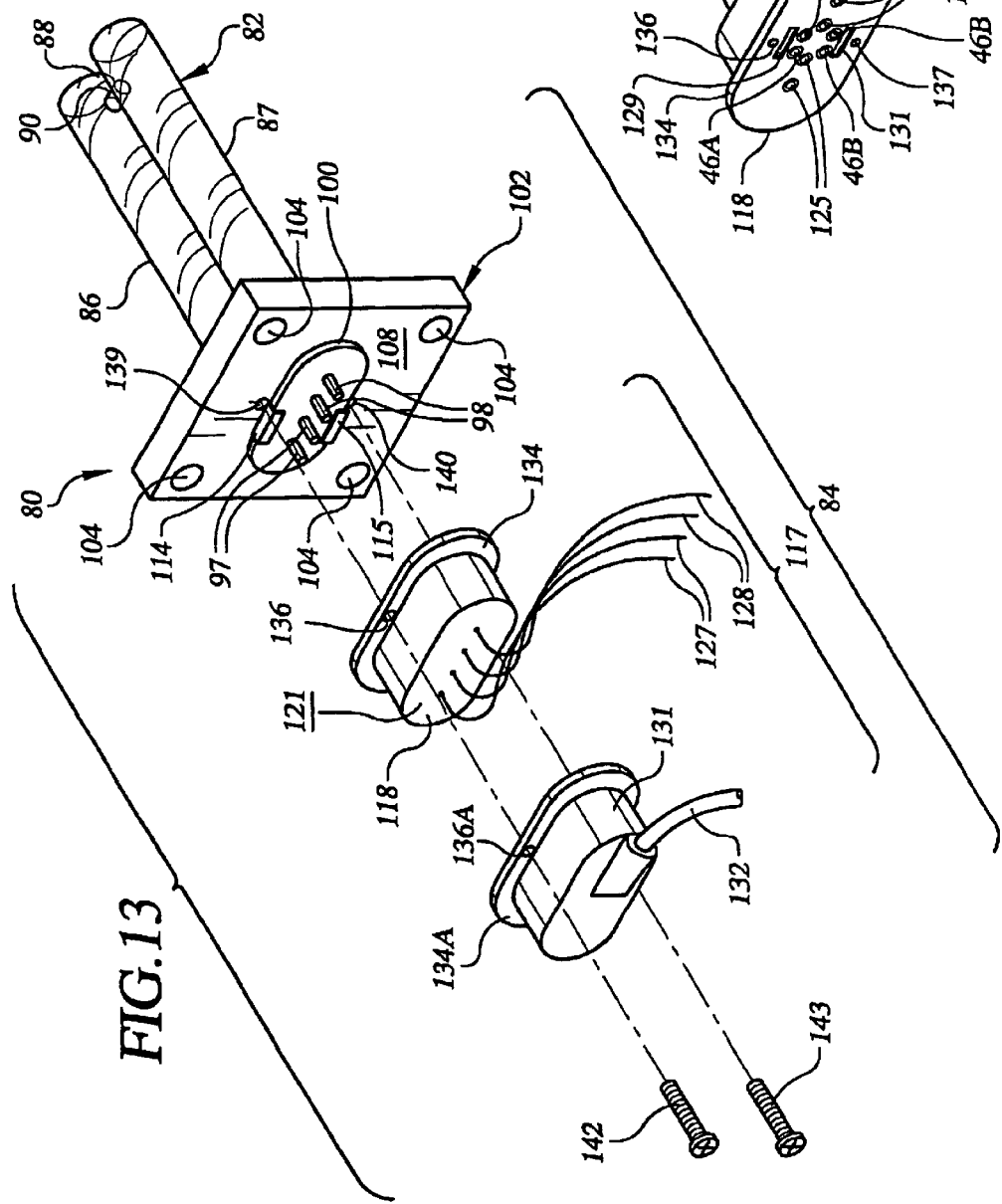
FIG. 13 is an exploded isometric perspective view of a radiation module 80 utilizing a twin tube radiation lamp 82 in accordance with yet another aspect of the invention.
Figure 14:
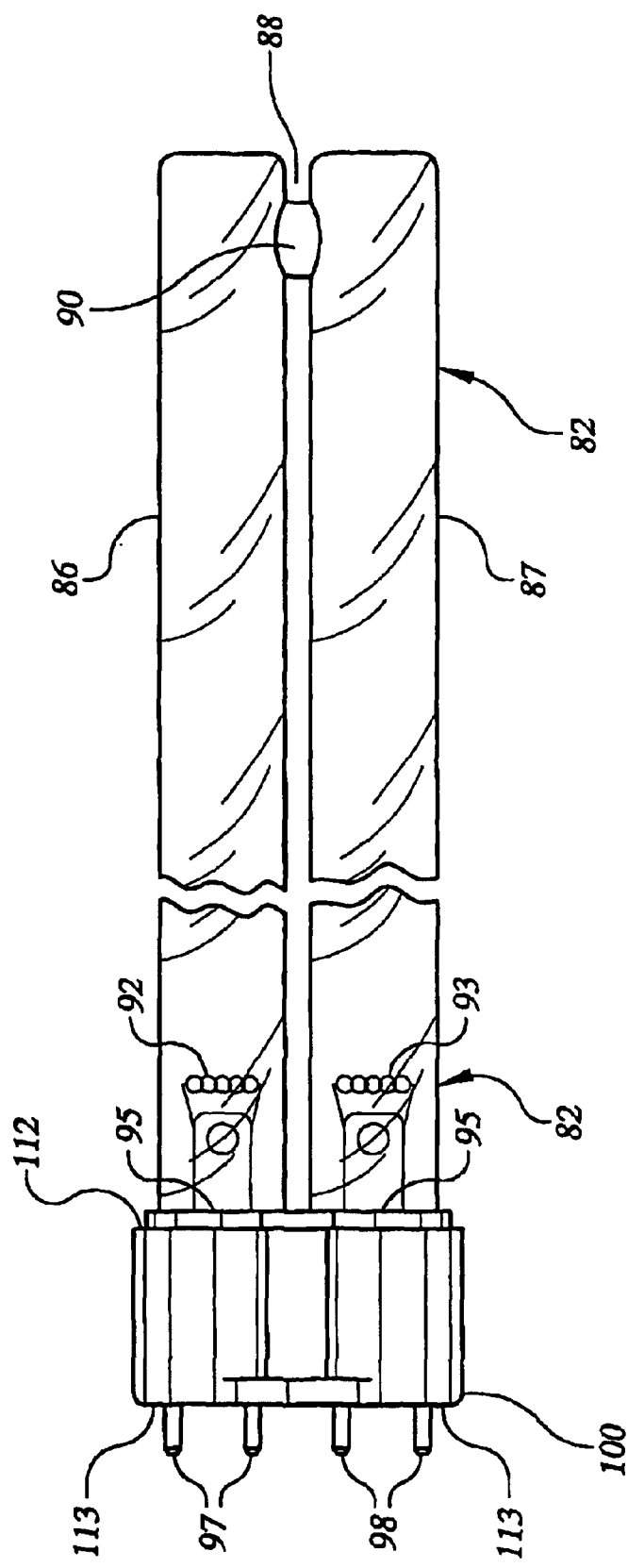
FIG. 14 is a detailed elevated plan view of the twin tube radiation lamp 82 illustrated in FIG. 13.

"Twin tube" lamps whose tubes are in a U-shaped configuration and mounted to a common lamp base for connection to a source of electrical power, may also be employed in the module according to the invention herein. Alternatively, the tubes may be aligned in a parallel fashion relative to each other and joined at the ends by a "crossover" section of tubing. As shown in FIG. 13, the opposite ends are also mounted to a common lamp base.

Other lamps include medium pressure ultraviolet lamps as well as capacitor discharge lamps that utilize pulse technology wherein a luminous output arises from the ionization in a gaseous discharge, examples of which include xenon lamps.

Figure 8:
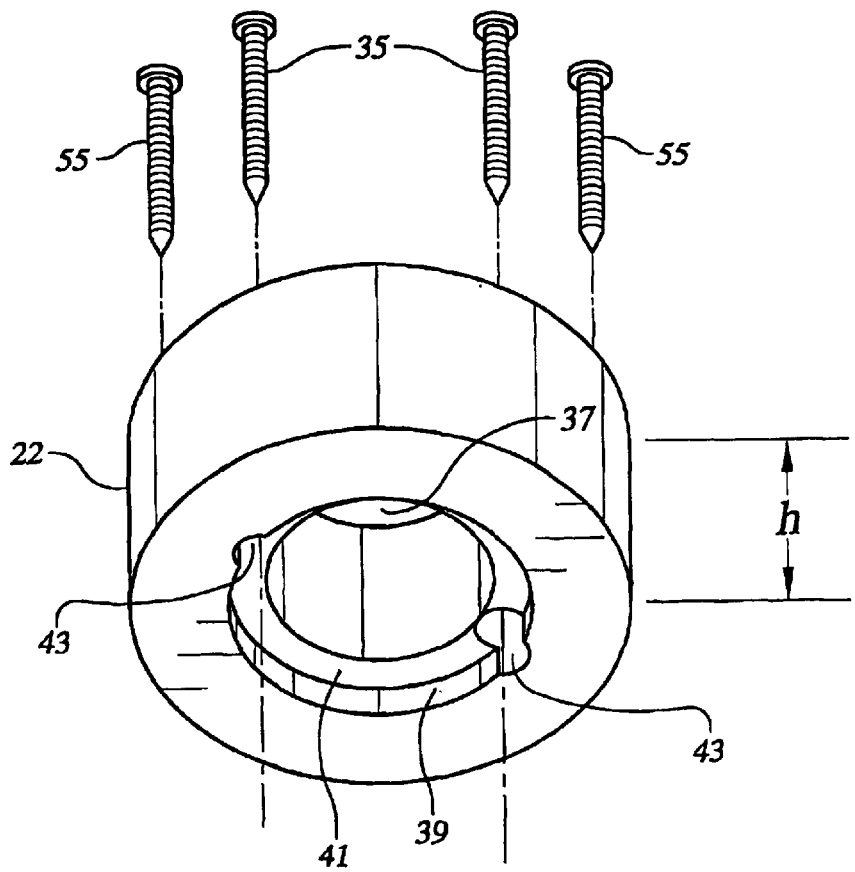
FIG. 8 is a isometric bottom view of the compression nut 22 illustrated in FIG. 2.
Figure 9:
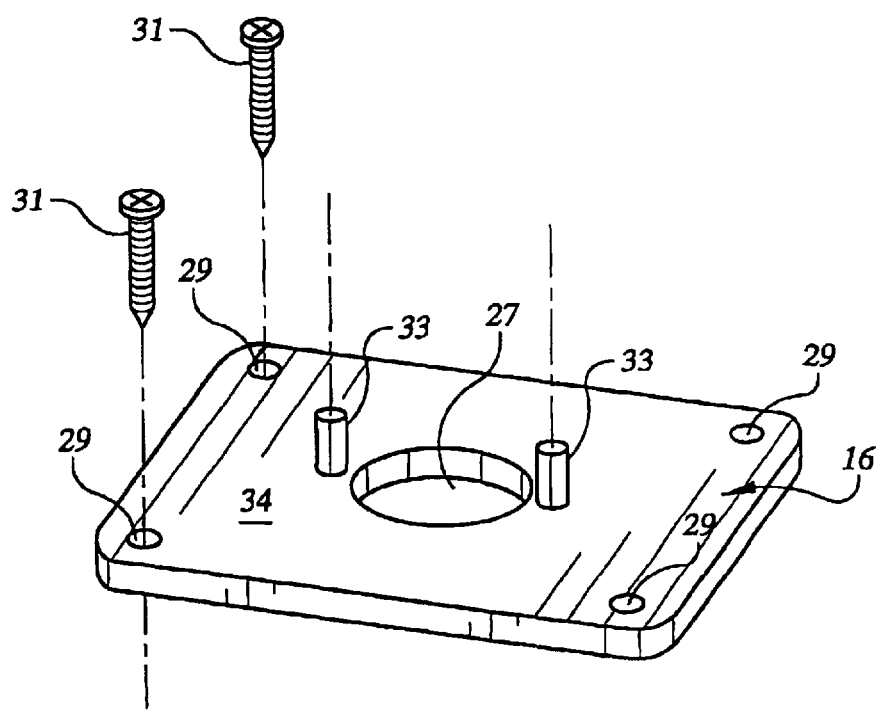
FIG. 9 is a isometric top view of the mounting plate 16 illustrated in FIG. 2.

As best illustrated in FIGS. 2, 4, 4A, and 9, and in accordance with one aspect of the invention, module 10, in addition to UV lamp 14, comprises a power disruption apparatus 11 for the disruption of power to the lamp that includes a mounting means in the form of mounting plate 16 that is mountable with the exterior surface 24 of duct 12 about duct opening 25. Mounting plate 16 is provided with an opening 27 for registry with duct opening 25 in order to accommodate the passage of UV lamp 14 therethrough into the interior of duct 12. Also provided are mounting apertures 29 for the insertion of fastening members which may take any form for the attachment of mounting plate 16 to the exterior surface 24 of duct 12, e.g., sheet metal screws 31 as shown, bolts, rivets, etc. As best shown in FIG. 9, mounting plate 16 additionally includes a pair of internally threaded bosses 33 mounted to the top side 34 of mounting plate 16 adjacent to opening 27 to receive correspondingly threaded fasteners in the form of threaded bolts 35 for attaching compression nut 22 (described below) to mounting plate 16 (see FIGS. 2, 4, 4A, 8 and 9).

Figure 5:
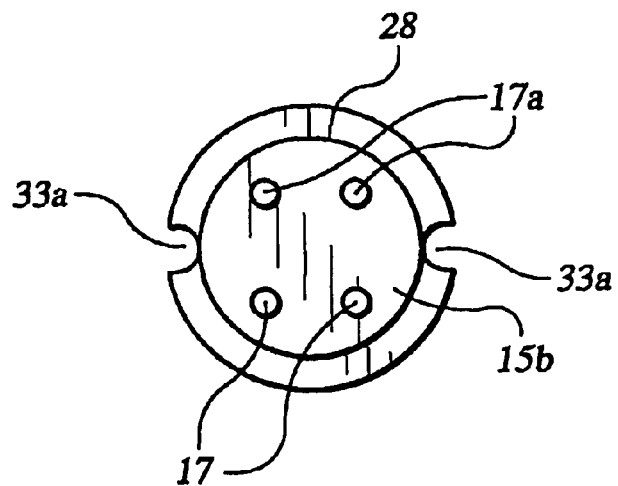
FIG. 5 is top plan view of the radiation lamp 14 illustrated in FIG. 6.

Referring now to FIGS. 4, 4A and 8, and more specifically to FIG. 8, a coupling member in the form of an annular compression nut 22 is provided whose annular opening 37 is sized to accommodate the receipt therethrough of the top portion 15b of lamp base 15. The lower annular wall 39 of compression nut 22 is undercut to provide an annular seat 41 that interfaces with a retention member in the form of flange 28 at the top side 26 thereof (see FIG. 7). Flange 28 is disposed about and secured to the exterior mid-section of lamp base 15 of UV lamp 14. Referring to FIGS. 5 and 9, apertures 33a are provided in flange 28 to accommodate the receipt therethrough of bosses 33 when UV lamp 14 is inserted through opening 27 of mounting plate 16 and the bottom surface 30 of flange 28 comes to rest upon and interfaces with the top surface 34 of mounting plate 16. This arrangement maintains lamp base 15 (as well as UV lamp 14) in a stationary position relative to exterior surface 24 of duct 12, and prevents UV lamp 14 from falling into the interior of duct 12.

Compression nut 22 is provided with fastener openings 43 for the insertion of fastening means for the securement of the nut to mounting plate 16. The height h of compression nut 22 (see FIG. 8) is sized such that when it is placed over lamp base 15 of UV lamp 14 and secured to mounting plate 16 using a fastening means, e.g., threaded bolts 35, terminal pins 17,17a of UV lamp 14 will extend beyond the top planar surface 44 of compression nut 22 (see FIGS. 4 and 4A) sufficiently to expose terminal pins 17,17a for engagement with corresponding electrical receptacles (not shown) contained within socket 20 (see FIGS. 4 and 11).

Figure 10:
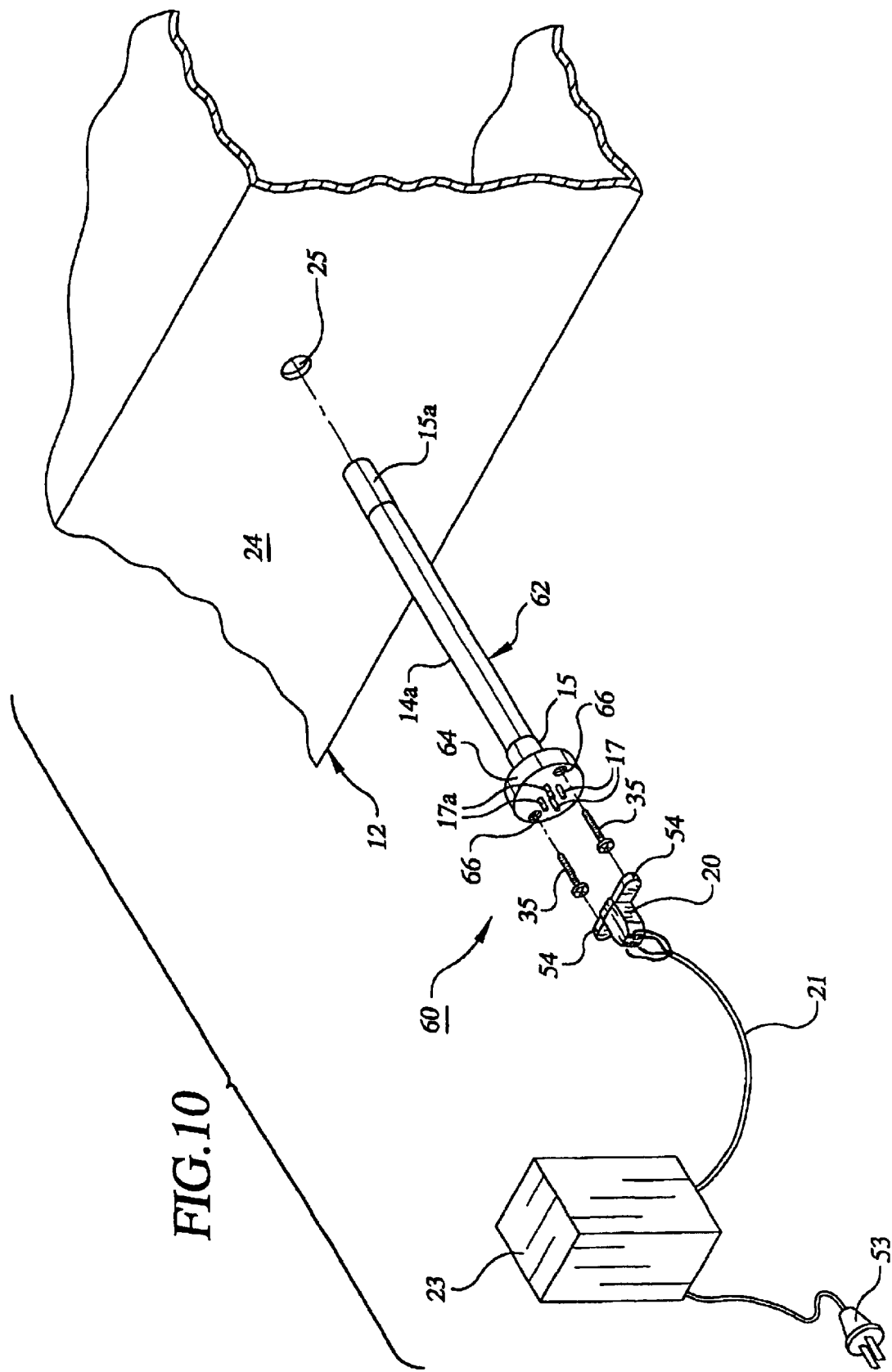
FIG. 10 is an exploded isometric view of a radiation module 60 before its incorporation with a HVAC duct in accordance with another embodiment of the invention.
Figure 11:
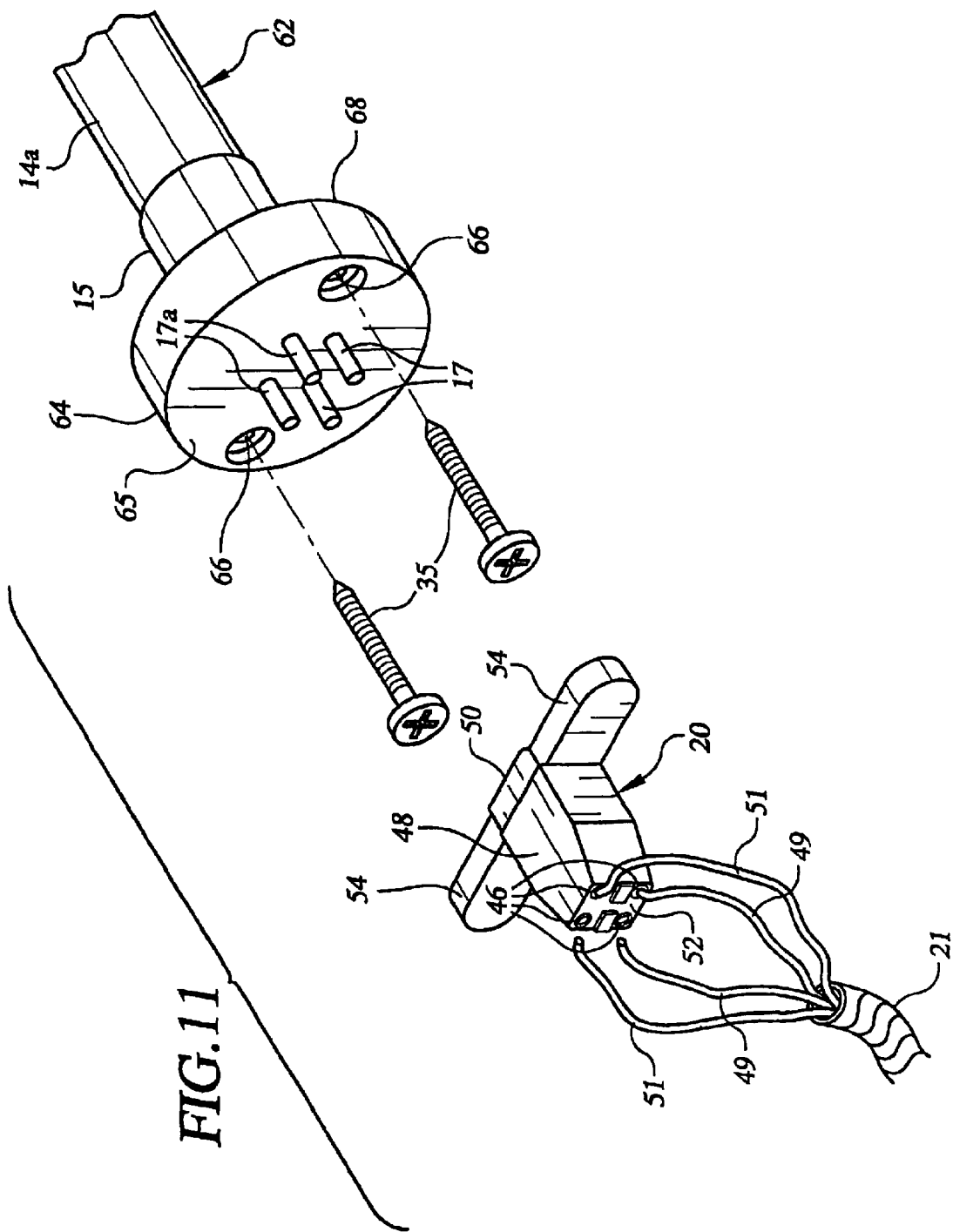
FIG. 11 is an enlarged detailed view of a portion of the radiation module 60 illustrated in FIG. 10.

Referring now to FIGS. 4, 4A and 11, the apparatus also includes an electrical coupling means that connects UV lamp 14 with an electrical power supply, e.g., a ballast 23 (see FIG. 10), for the lamp's operation. The electrical coupling means may, for example, take the form of an electrical coupling member comprising a socket 20 having an elongate section 48 that has a front end 50 and an opposite tapered end 52 (see FIGS. 4 and 11). Embedded within socket 20 about the front end 50 are four electrical receptacles (not shown) about end 50 that interface with and receive with a resistance fit the terminal pins 17,17a axially extending from the top portion 15b of lamp base 15. The opposite end 52 is provided with four openings 46 for receiving two pairs of electrical transmission wires 49 and 51 which are secured at one end thereof to the respective electrical receptacles within socket 20 that receive terminal pins 17,17a. For convenience, electrical transmission wires 49,51 are carried within cable 21. As shown in FIG. 10, the opposite ends of electrical transmission wires 49,51 are electrically connected via cable 21 to ballast 23. It will be appreciated that the electrical receptacles embedded within socket 20 can be extended over the length of elongate section 48 to interface back end 52 of socket 20 to provide a female-to-female socket. In this embodiment the electrical receptacles (not shown) may be adapted to interface with and receive with a resistance fit the electrical pins of a mateable male plug (not shown), the latter being electrically connected to ballast 23 via electrical transmission cable 21.

As illustrated in FIG. 11, the electrical coupling member is also configured in a manner to obstruct access to the fasteners that detachably secure compression nut 22 to mounting plate 16. Accordingly, an obstruction element is provided for the electrical coupling member, in this case side extensions 54 disposed on opposite sides of elongate section 48 about end 50, for overlying the heads of threaded bolts 35. The primary function of side extensions 54 is to prevent access to the fastening means, i.e., threaded bolts 35, which detachably secure compression nut 22 to mounting plate 16. As a secondary function, side extensions 54 may optionally be provided with openings 56 (FIGS. 4 and 4A) to receive fastening means in the form of threaded fasteners 55 for additional detachable securement of socket 20 with compression nut 22. As shown in FIG. 8, threaded fasteners 55 may be in the form of screws or threaded bolts which are inserted through openings 56 for engagement with aligned openings 58 (see FIG. 4A) of compression nut 22. It will be appreciated that socket 20 may be configured in any manner that provides an electrical connection with terminal pins 17,17a of UV lamp 14 while simultaneously preventing access to the fastener, e.g., threaded bolts 35, which detachably secures compression nut 22 with mounting plate 16.

Figure 12:
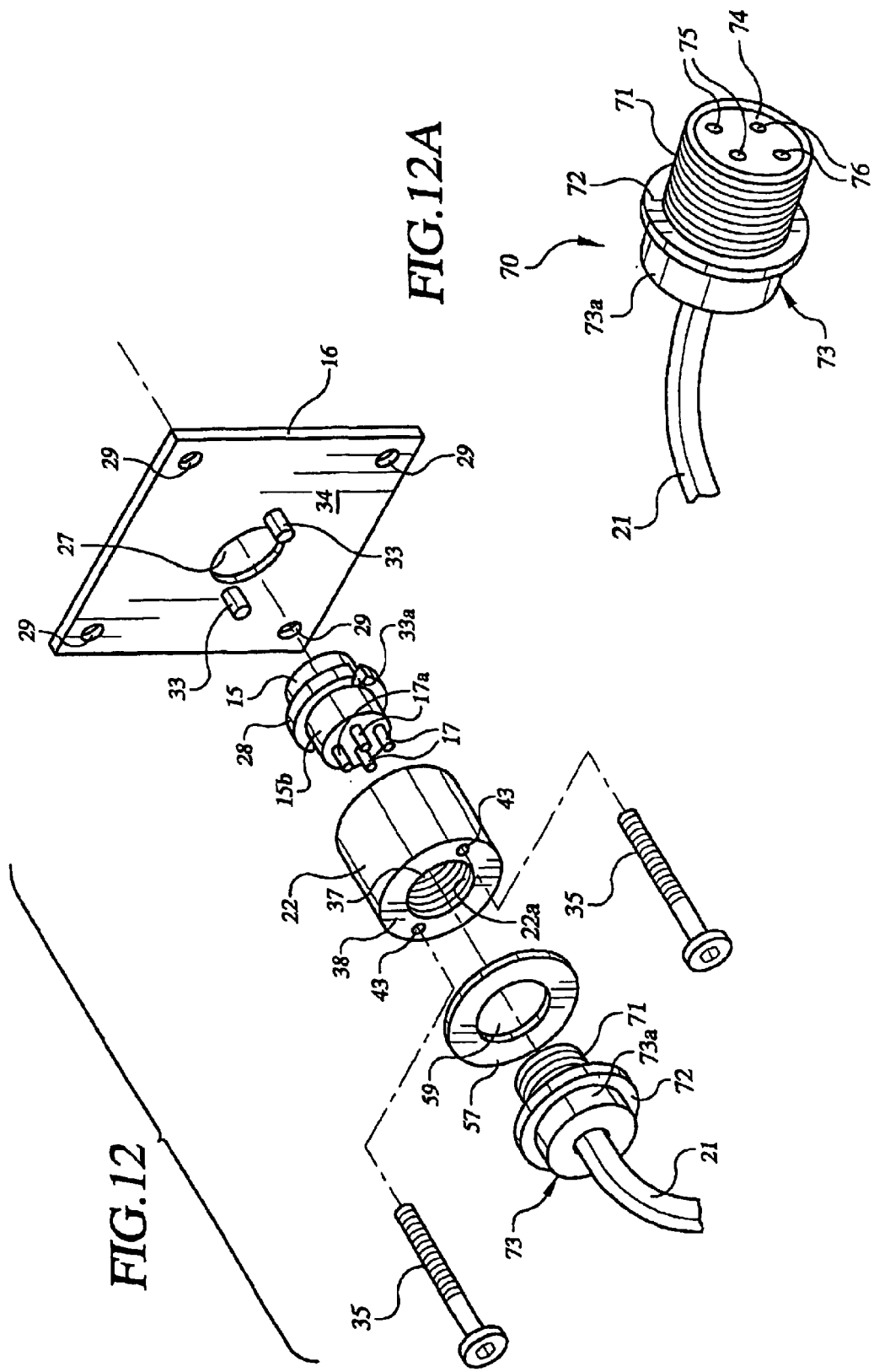
FIG. 12 is an enlarged exploded isometric view of a portion of a radiation module in accordance with another aspect of the invention.

As an alternative to side extensions 54, and as shown in FIG. 12, a properly configured annular member 57 may be interposed between compression nut 22 and socket 20 in order to prevent access to threaded bolts 35 which secure compression nut 22 to mounting member 16. In this embodiment, the annular opening 59 of annular member 57 is sized such that the exposed portion of terminal pins 17,17a will have full penetration into the corresponding receptacles at end 50 of socket 20.

As an alternative to the configuration of socket 20 in the foregoing apparatus and module, FIG. 12 illustrates another embodiment for an electrical coupling member. Referring to FIG. 12A, the electrical coupling 70 comprises an electrical socket 74 that retains a pair of electrical receptacles 75,76 the ends of which are connected with electrical transmission wires 49,51 (see FIG. 11) carried by cable 21. The opposite open ends of electrical receptacles 75,76 are disposed within the socket for receiving terminal pins 17,17a of lamp base 15 with a resistance fit. Mounted about socket 74 is a freely rotating housing 73 that includes an exteriorly threaded, annular extension 71 and a non-threaded extension 73a axially extending from either side of a flange 72. The housing 73 is mounted about socket 74 and the end portion of cable 21 such that it is free to rotate about cable 21 and socket 74, but is axially fixed to cable 21 about the end thereof. Extension 71 is configured for threaded engagement with the correspondingly threaded annular interior 22a of compression nut 22 shown in FIG. 12.

Assembly of electrical coupling 70 with UV lamp 14 is as follows. After compression nut 22 is placed over top portion 15b of lamp base 15 and secured to mounting plate 16 by the insertion of threaded bolts 35 through openings 43, annular member 57 is placed over the annular planar surface 38 of compression nut 22 to prevent access to threaded bolts 35. The electrical receptacles 75,76 of socket 74 contained within electrical coupling member 70 is then mated with terminal pins 17,17a simultaneously with the insertion of extension 71 through the annular opening 59 of annular member 57. Flange 72 is rotated for threaded engagement of threaded extension 71 with the interior of compression nut 22 to complete the connection.

Assembly of the radiation module 10 illustrated in FIG. 4 and its incorporation with duct 12 to provide an air disinfection assembly, is accomplished by securing mounting plate 16 to duct 12 in a manner that the opening 27 in mounting plate 16 (see FIG. 9) and the opening 25 of duct 12 (see FIG. 10) are in direct alignment with each other. Lamp base 15a of UV lamp 14 is then inserted through openings 27 and 25 to a point where the bottom surface 30 of flange 28 interfaces with the top surface 34 of mounting plate 16. Once UV lamp 14 is in place, compression nut 22 is fitted over the extended top portion 15b of lamp base 15 and the compression nut attached to mounting plate 16 by a fastening means, in this case by the engagement of threaded bolts 35 with bosses 33 as shown in FIG. 9. Stationary securement of UV lamp 14 with duct 12 is thereby obtained. UV lamp 14 is coupled with a source of electrical power by aligning the electrical receptacles of socket 20 over pins 17,17a of the top portion 15b of lamp base 15 for insertion of the pins therein. As illustrated in FIGS. 10–11, electrical transmission wires 49 and 51, which connect with the respective electrical receptacles within socket 20, are electrically connected via cable 21 to ballast 23 to complete the incorporation of radiation module 10 with HVAC duct 12.

With the foregoing power disruption apparatus integrated with UV lamp 14 and HVAC duct 12, removal of UV lamp 14 from duct 12 can only be achieved by the disruption of electrical power to the lamp. Accordingly, when circumstances warrant the removal of UV lamp 14 from duct 12, e.g., for cleaning the lamp's surface or simply to replace the lamp, socket 20 must first be disconnected from compression nut 22. This is accomplished by either removing the threaded fasteners 55 (see FIG. 8) from the respective side extensions 54 of socket 20 (FIG. 4A), or if the threaded bolts 55 are not utilized as in FIG. 11, by simply uncoupling the socket 20 from the terminal pins 17,17a of UV lamp 14. Once removed, threaded bolts 35, which secure compression nut 22 to mounting plate 16, will be accessible for their removal from the compression nut 22 and the bosses 33 of mounting plate 16. As a consequence of the foregoing process, the power to UV lamp 14 is totally disrupted before its removal from HVAC duct 12, and compression nut 22 can be lifted off the top portion 15b of lamp base 15 and the lamp safely withdrawn. The lamp's withdrawal from duct 12 can only be accomplished by decoupling socket 20 from the terminal pins 17,17a of UV lamp 14.

In accordance with another aspect of the invention, FIGS. 10–11 show a modified power disruption apparatus and radiation module. It will be appreciated that all parts illustrated in FIGS. 10 and 11 and those Figures that follow, which are identical with or clearly analogous to the corresponding part of the apparatus and module shown in FIGS. 1–9, are denoted by like reference numerals and characters.

Figure 18:
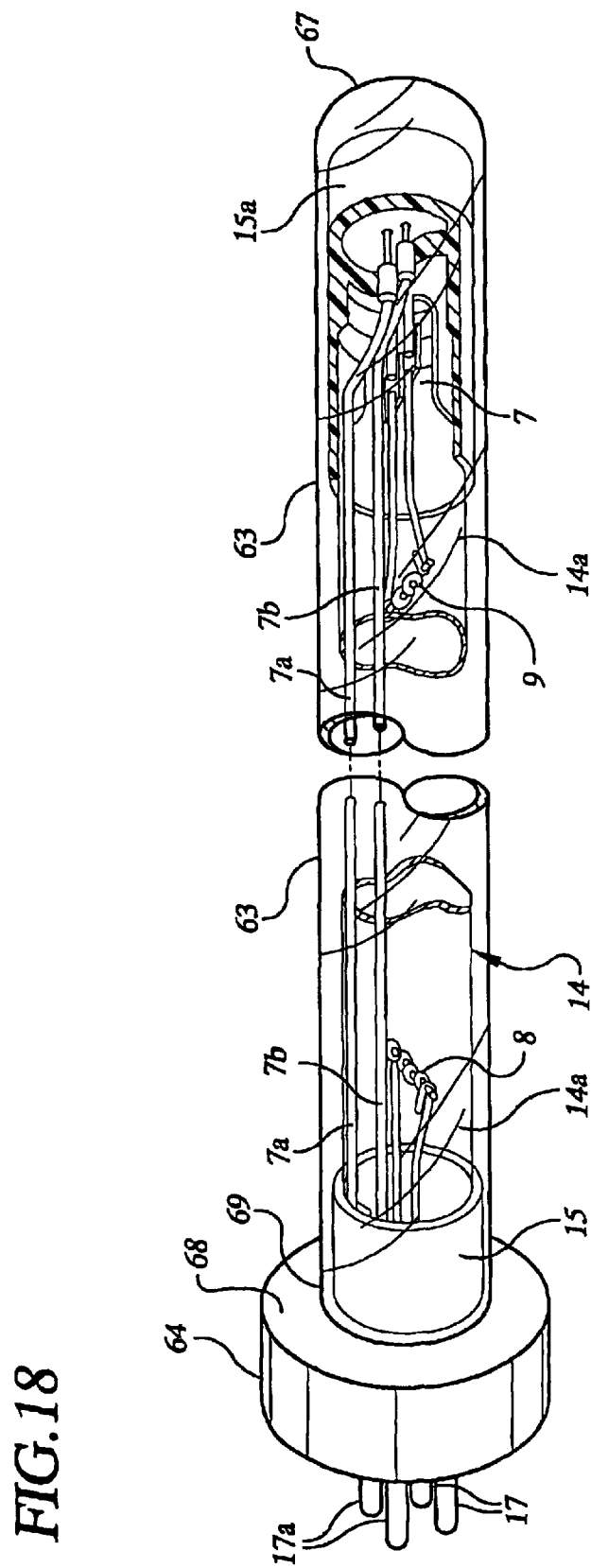
FIG. 18 is a segmented isometric view of the radiation lamp 62 illustrated in FIG. 10 with the inclusion of a protective quartz sleeve 63.

Referring to FIG. 10, radiation module 60 is comprised of a radiation source, e.g., in the form of UV lamp 62, an electrical coupling member, e.g., socket 20, and a mounting member 64 for securing one end of UV lamp 62, i.e., the end carrying terminal pins 17,17a, to the surface 24 of duct 12. As shown in greater detail in FIG. 18, reference numeral 62 designates a low pressure ultraviolet radiation lamp comprising a vacuumed tubular portion 14a that is sealed at each end thereof in the same manner illustrated in FIG. 6. Both tubular ends 6 and 7 of UV lamp 62 are retained and supported by lamp bases 15 and 15a, respectively. Secured about the end portion of lamp base 15, and made integral therewith, is a mounting member 64 of ceramic or plastic construction whose cross-sectional area is configured to be sufficiently larger than duct opening 25 so as to maintain the mounting member exteriorly of duct 12 when UV lamp 62 is inserted into the duct interior via opening 25. Lamp base 15 can be made integral with mounting member 64 in any number of ways, for example by providing a bore within the mounting member for defining a seat that the end of lamp base 15 butts against when inserted into the mounting member. The bore within mounting member 64 is accompanied by axially extending apertures through the mounting member for exposure of the terminal pins 17,17a beyond the member's planar surface 65 (see FIG. 11). Alternatively, mounting member 64 can be configured as an annular element whose annular opening is sized to slidably receive lamp base 15 therein. In either configuration, lamp base 15 may be retained within mounting member 64 by the application of an appropriate fixative or sealant, e.g., an ultraviolet light curative epoxy cement available from Norland Products Inc. under the name of Norland Electronic Adhesive, between the mounting member's bore or inside annular surface, as the case may be, and the outside surface of lamp base 15. Mounting member 64 and lamp base 15 can also be configured into a single or unitary structure for carrying the terminal pins 17,17b to support the end 6 (see FIG. 6) of lamp tubing 14a while functioning as a flange relative to surface 24 of duct 12. While mounting member 64 is illustrated in FIGS. 11 and 18 as having a circular cross-section, it may be configured in any shape or form to act as an interface with the exterior surface 24 of duct 12, typically in the form of a flange.

The mounting member 64 of lamp base includes a plurality of apertures (not shown) to accommodate the insertion of terminal pins 17,17a emanating from lamp base 15, the terminal pins extending in the axial direction beyond the planar surface 65 of mounting member 64 for available electrical connection with female-to-female socket 20. Also included within mounting member 64 are a pair of countersunk fastener openings 66 to accommodate the insertion of threaded bolts 35 therein for securing mounting member 64 to the surface 24 of duct 12 about opening 25. The integration of mounting member 64 with lamp base 15, terminal pins 17,17a and the remainder of lamp 62, provides a simplified and economical means for incorporating UV lamp 62 with duct 12. Alternatively, it will be appreciated that mounting member 64 may be annularly configured and secured about the end of lamp base 15, i.e., the end portion of lamp base 15 will be inserted into an annular opening of the mounting member and secured therewith by any conventional means.

As shown in FIG. 10, once lamp base 15a of UV lamp 62 is inserted through duct opening 25 to a point where the surface 68 of mounting member 64 interfaces with the exterior surface 24 surrounding opening 25 of duct 12, end 50 of socket 20 is fitted over the exposed terminal pins 17,17a of mounting member 64 for receiving them into the electrical receptacles contained within the socket. Electrical transmission wires 49,51 are electrically connected via cable 21 between the opposite ends of the electrical receptacles in socket 20 (via openings 46) and ballast 23 to complete the electrical coupling of lamp 62 to the ballast. As with radiation module 10, and the apparatus illustrated in FIGS. 1–9 and described hereinbefore, the side extensions 54 of socket 20 will cover openings 66 and threaded bolts 35 already inserted into mounting member 64. This arrangement prevents the removal of lamp 62 from duct 12 unless socket 20 is decoupled from pins 17,17a of UV lamp 14. With this embodiment of the invention, the functions of mounting plate 16, compression nut 22 and lamp base 15 of module 10 are integrated into a unitary structure.

FIGS. 13–16 illustrate yet another embodiment of the invention herein. Referring to FIG. 13, radiation module 80, like radiation modules 10 and 60, comprises a "twin-tube" UV lamp 82 and a power disruption apparatus 84. As shown in greater detail in FIG. 14, UV lamp 82 comprises two hollow elongate quartz tubes 86,87 that are parallel to each other along their longitudinal lengths, and joined together about one end 88 of lamp 82 by a short hollow connecting tube 90. The electrodes 92,93 of the respective tubes 86,87 are disposed at the opposite ends 95 of the lamp tubes, and are connected respectively, via lead wires (not shown), with terminal pins 97,98 carried by and axially extending from a common lamp base 100.

Figure 16:
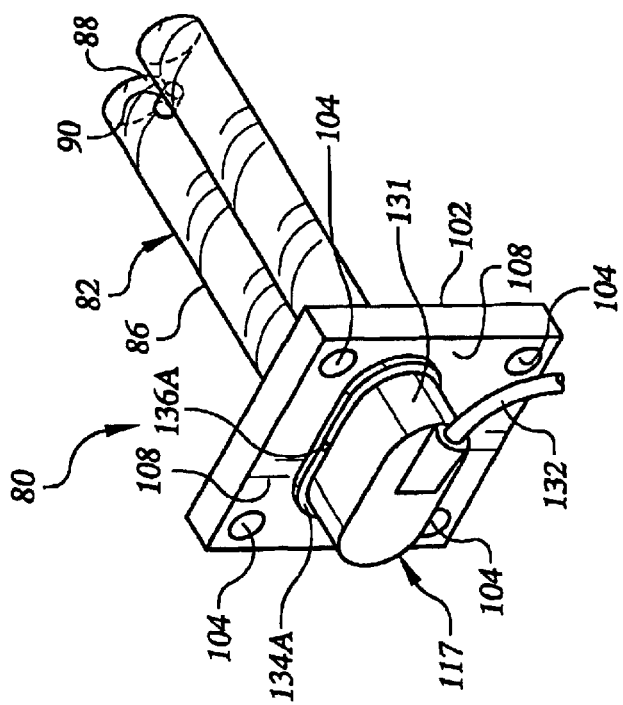
FIG. 16 is an isometric view showing the assembly of radiation module 80 illustrated in FIG. 13.
Figure 15:
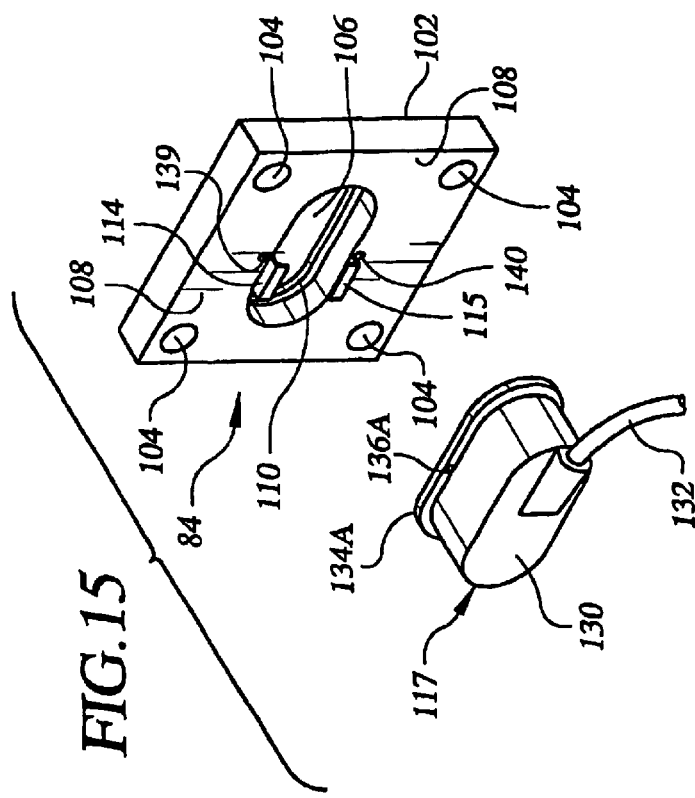
FIG. 15 is a partially exploded isometric view of the power disruption apparatus 84 illustrated in FIG. 13 without the inclusion of twin tube radiation lamp 82.

Power disruption apparatus 84 comprises a mounting member 102 provided with fastener openings 104 for securement of the member to the exterior surface 24 of duct 12 utilizing a fastening means, e.g., screws or threaded bolts (not shown). As shown in greater detail in FIG. 15, a centrally positioned opening 106 provided in the mounting member is configured to receive quartz tubes 86,87 of UV lamp 82 therethrough (as shown in FIG. 16). It will be understood that when mounting member 102 is attached to duct 12, opening 106 will register with a similar opening provided in the wall of duct 12 (not shown) to receive UV lamp 82 into the interior of the duct. As best shown in FIG. 15, the front side 108 of mounting member 102 is undercut to provide a seat 110 that interfaces with the back end 112 of lamp base 100 (see FIG. 14) for defining a flange for UV lamp 82 when it is inserted through mounting member opening 106. In order to maintain the lamp in place, releaseable locking means, e.g., resilient retainer clasps 114,115 which have a spring bias in a direction pointing to the center of opening 106, are disposed about the perimeter of opening 106 on the front side 108 of mounting member 102. As shown in FIG. 13, when UV lamp 82 is sufficiently inserted into duct 12, the spring bias of retainer clasps 114,115 will exert themselves against the front side 113 of lamp base 100 and lock the lamp base within opening 106 of mounting member 102. In this manner, one end of lamp base, i.e., end 112, serves as a lip that interfaces with seat 110 of mounting member 102, and cooperates with the front or opposite side 113 of lamp base 100 to provide a locking mechanism for securing the lamp to duct 12.

In order to supply electrical power to UV lamp 82 from a source external to module 80, and as illustrated in greater detail in FIG. 13, an electrical coupling member, e.g., female socket assembly 117, is employed as part of the power disruption apparatus 84. As best shown in FIGS. 13 and 13A, female socket assembly 117 comprises a socket 118 having front and rear sides 121 and 122, respectively, the socket being made of ceramic, plastic or similar solid dielectric material, and being overlaid with an optional dielectric boot 131. Socket 118 is sized and configured to accommodate the containment of electrical receptacles 124, 125 that register with and receive terminal pins 97,98 of lamp 82, respectively, which project from lamp base 100. One end of electrical receptacles 124,125 terminates at the planar surface of the casing's rear side 122, while their opposite ends are respectively connected with electrical conductor wires 127 and 128 emanating from the front side 121 of socket 118. The electrical conductor wires 127, 128 are collectively housed in an insulated cable for connection to an electrical power source. Disposed about the periphery of socket 118 is a joining member in the form of a circumferential lip 134 that includes openings 136,137 (FIG. 13A) for affixing female socket 118 to the front side 108 of mounting member 102. Mounting apertures 139,140 are provided in mounting member 102 for receiving attachment screws 142,143 therein through openings 136,137. Socket 118 additionally includes slotted indentations 129,131 (FIG. 13A) to accommodate the receipt of resilient retainer clasps 114,115, respectively, when the rear side 122 of the socket is interfaced with the front side 113 of lamp base 100.

Female socket assembly 117 may optionally include a dielectric boot 131 made of a flexible insulating material that is sized and configured to receive socket 118 therein. Boot 131 also includes an electrical insulating cable 132 for receiving and carrying conductor wires 127,128 to an electrical power source, e.g., ballast 23 which is illustrated in FIG. 10. Attached about or integral with the periphery of boot 131 is a joining member in the form of a circumferential lip 134A that is configured to overlie circumferential lip 134 of socket 118. Circumferential lip 134A includes openings 136A,137A for registry with the openings 136,137 in lip 134 (see FIG. 13A) to accommodate the insertion of attachment screws 142,143 therethrough.

Assembly of radiation module 80 is best illustrated in FIGS. 13, 15 and 16. Retainer clasps 114,115 are manually pushed in a direction away from the center of opening 106 of mounting member 102, and UV lamp 82 simultaneously inserted into opening 106 until the back end 112 of lamp base 100 butts against seat 110 of mounting member 102. Thereafter, retainer clasps 114,115 are released to lock lamp base 100 within mounting member 102. Electrical receptacles 124,125 of socket 118 are then aligned and coupled with terminal pins 97,98, respectively, which has the effect of preventing access to retainer clasps 114,115 by circumferential lip 134. As best seen in seen in FIG. 13, securement of female socket assembly 117 and its boot 131 to the terminal pins 97,98 of UV lamp 82, is insured by inserting attachment screws 142,143 through the respective openings 136 and 136A of circumferential lips 134 and 134A, respectively, into the corresponding mounting appertures 139,140 of mounting member 102.

With the assembly of radiation module 80 complete, the module may be incorporated with duct 12 by inserting lamp end 88 into the opening (not shown) of duct 12 and securing mounting member 102 thereto by the use of fastening means, e.g., mounting screws (not shown), inserted into openings 104 and into the wall of duct 12. Alternatively, the assembly of radiation module 80 can be undertaken simultaneously with its incorporation with duct 12. Mounting member 102 may initially be fixed to duct 12 by registering opening 106 with the corresponding opening (not shown) provided in the duct wall, and then securing the mounting member to the duct wall in the manner described above. Once mounting member 102 is secured in its proper place with duct 12, the remainder of module 80 is assembled by first inserting lamp end 88 into the duct interior and locking the lamp base 100 with the mounting member via retainer clasps 114,115. With the terminal pins 97,98 of UV lamp 82 exposed, their connection with an electrical power source is accomplished by coupling them with the appropriate electrical receptacles 124,125 of female socket assembly 117, and then insulating cable 132 with an electrical power supply, e.g., ballast 23 as shown in FIG. 10. As described above, securement of female socket assembly 117 to mounting member 102 is assured by the use of attachment screws 142,143 inserted through the respective openings 136,136A of circumferential lips 134,134A and into the corresponding mounting apertures 139,140 of mounting member 102.

Figure 2:
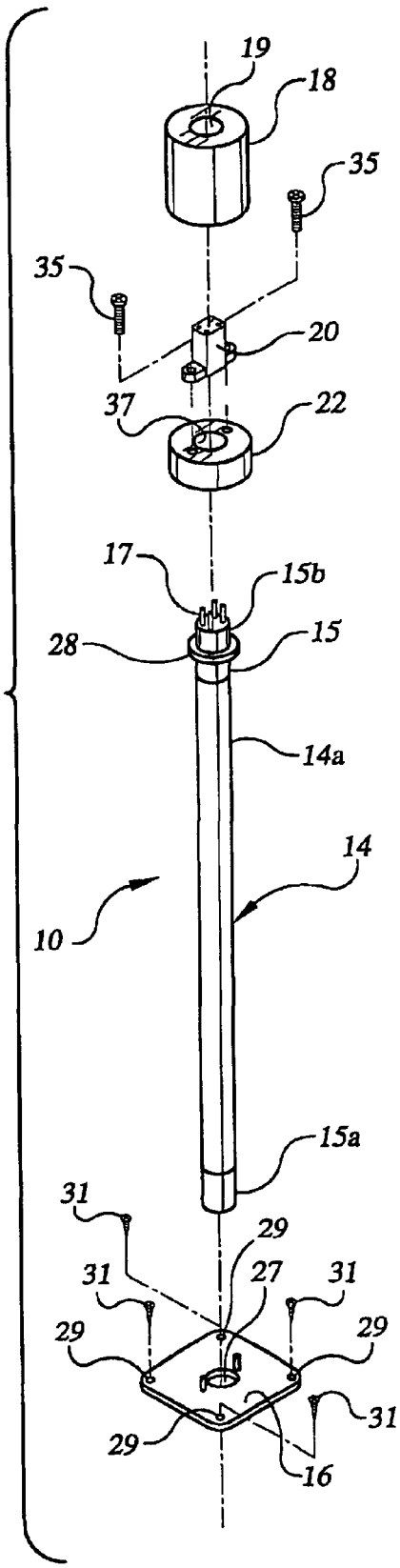
FIG. 2 is an exploded isometric view of the radiation module 10 illustrated in FIG. 1 illustrating the assemblage of the individual components of the module.
Figure 17:
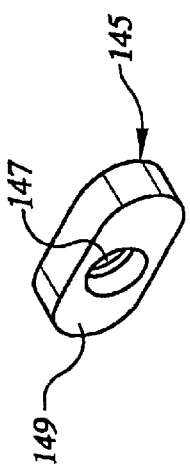
FIG. 17 is an isometric view of an adapter component for modification of the power disruption apparatus 84 illustrated in FIG. 15.

Referring now to FIG. 17, interchangeability of twin-tube UV lamp 82 with, for example, a single tube lamp such as UV lamp 14 illustrated in FIGS. 2 and 6, is made possible by the incorporation of an adapter 145 with mounting member 102. Adapter 145, which is configured in size and shape to fit within opening 106 of mounting member 102, itself contains an opening 147 for receiving UV lamp 14 therethrough. Once inserted, and as illustrated in FIG. 15, the back side (not shown) of adapter 145 interfaces with and rests upon seat 110 (see FIG. 15) of mounting member 102. Adapter 145 is held in place within mounting member 102 by the insertion of UV lamp 14 into opening 147 whereupon the bottom surface 30 of flange 28 (see FIGS. 2 and 7) will interface with the front side 149 of adapter 145.

As shown in FIG. 13A, and in order to secure UV lamp 14 in place, the electrical receptacles 46A,46B of female socket assembly 117 are then fitted over terminal pins 17,17a of the extended portion of lamp base 15, and secured to mounting member 102 in the same manner as that illustrated in FIGS. 13 and 16.

In another embodiment of the invention, the radiation modules described herein include the incorporation of a radiation pervious protective sleeve mounted about the radiation lamp to stabilize the operating temperature of the inner and outer portions of the lamp tubing when it is subjected to temperature fluctuations of the air being passed through an HVAC duct. HVAC duct systems generally operate by admitting air from an outside environment and then subjecting it to filtration, cooling and/or heating, and humidification, and finally transporting it via a duct system to a plurality of rooms or spaces such as offices and living, commercial and industrial spaces, or vehicles such as automobiles and public transport vehicles, e.g., airplanes, buses, trains, etc. The longevity and efficiency of UV lamps used in HVAC systems are generally dependant upon the temperature of the duct air that they are exposed to. UV lamps will operate at maximum efficiency when the temperature of the lamp's exterior tubular surface is maintained at a range of from 103° F. to 110° F., with peak efficiency being obtained at approximately 105° F. Contributing factors toward the lamp's operational efficiency include a proper matching of the lamp with a ballast or power source, i.e., the electrical characteristics of the lamp and ballast should complement each other. For example, if the UV lamp is underpowered, the optimum 105° F. operating temperature may not be achieved. If the UV lamp is overpowered, i.e., operated at an amperage beyond the recommended specification for the lamp in question, it will usually result in premature lamp failure or solorization of the lamp, thereby shortening the lamp's useful life. Solorization is the process by which UV lamps lose the ability to generate ultraviolet energy in the UVC radiation wavelength range over a period of time. This is due to the lamp's mercury becoming embedded into the interior of the glass tubing which leads to mercury loss and contributes to the UV lamp's inefficiency and shortened life span.

Another contributing factor is heat removal from the lamp's operation. This is borne out by the graph in FIG. 19 which charts the radiation energy (in ultraviolet micro-watts per square centimeter, measured at a distance of one foot from the lamp) of a 4-pin, low pressure, industry standard ultraviolet lamp [gph357t5/L] manufactured by First Light Technologies Inc. of Poultney, Vermont. The UV lamp was positioned within an air duct and operated at duct air temperatures ranging from 42° F. to 65° F. The graph demonstrates that as the duct air temperature increases, an increase in operating efficiency is experienced by the UV lamp in an amount of approximately 50 percent (see the lower line representation in FIG. 19). This contrasts with the efficiency experienced by the UV lamp when a radiation pervious protective sleeve, typically constructed of fused quartz, is placed over the same lamp (as illustrated in FIG. 18) and subjected to the same operating conditions. The upper line shows more than an 80 percent increase in ultraviolet micro-watts at the lower end of the temperature range (42° F.) and a slight increase in micro-watt output when the air duct temperatures rise above 57° F.

While not being bound to any specific theory or explanation, it is believed that the cooler duct air temperatures will lower the skin temperature of the lamp's tubing, and in turn, the inside operating temperature of the lamp. This lowering of temperature causes the mercury vapor pressure inside the lamp to drop which leads to the production of less ultraviolet light. Moreover, as heat is drawn away from the UV lamp by the colder duct air, the operating longevity of the lamp suffers significantly.

Referring now to FIG. 18, UV lamp 62, which is the same as that illustrated in FIG. 11, is enclosed by a radiation pervious protective sleeve. The sleeve is typically constructed of fused quartz, although any of the ultraviolet pervious materials such as Kynar® or Teflon may be used. Thus, quartz sleeve 63 has a closed dome-shaped configuration at one end 67 and is open at its opposite end 69. The open end 69 is sized to slidably fit about the circumference of lamp base 15 and interface with the back surface 68 of mounting member 64. Quartz sleeve 63 is fixed in place by the application of an appropriate fixative or sealant, e.g., an ultraviolet light curative epoxy cement available from Norland Products Inc. under the name of Norland Electronic Adhesive, between the inside surface of the sleeve's open end 69 and the outside surface of lamp base 15, between the open end 69 of the sleeve and the back surface 68 of the mounting member, or by an application to both areas.

Alternatively, and as described hereinbefore, mounting member 64 may be provided with an axial bore the end of which defines a seat that the end of lamp base 15 butts against when the lamp is inserted into the mounting member. In order to accommodate the inclusion of quartz sleeve 63, the size of the bore may be configured such that both ends of lamp base 15 and quartz sleeve 63 are slidably received within the bore and fastened to the seat of the bore with the appropriate fixative. Alternatively, a "stepped bore" may be incorporated in mounting member 64 to define a seat for the end of lamp base 15 and a separate higher seat for the open end 69 of quartz sleeve 63.

Quartz sleeve 63 may also be included with the other modular embodiments described hereinbefore. For example, referring to FIG. 7, the inside open end 69 of quartz sleeve 63 may be slidably fitted onto lamp base 15 and secured to the outer surface of the lamp base as well as the bottom surface 30 of flange 28. A similar arrangement may be followed with the lamp base 15 and flange 28 illustrated in FIG. 12. And in FIG. 12, the opening 27 of mounting member 16 is sized to accommodate the receipt therethrough of quartz sleeve 63 surrounding and fixed to lamp base 15 beneath flange 28. The incorporation of a quartz sleeve with a UV lamp in accordance with the invention herein serves to balance the temperature of the lamp, and by doing so, optimum performance, coupled with increased longevity, is achieved.

Since other modifications and changes may be varied to fit the particular operating requirements and environments of the invention, which will be apparent to those skilled in the art, the invention is not considered to be limited to the embodiments chosen for purposes of disclosure, and covers all changes and modifications which do not constitute departures from the true spirit and scope thereof.

What is claimed is:

1. An air disinfection assembly comprising a radiation module for incorporation with a conduit containing the passage of air therethrough, said module comprising:
   a radiation lamp for generating ultraviolet light including a lamp base that supports (i) at least one lamp tubing at one end thereof, (ii) a plurality of axially extending electrical terminal pins, and (iii) a flange disposed about the circumference thereof; and
   a power disruption apparatus comprising
   a mounting member provided with an opening that registers with an opening in said conduit when said mounting member is detachably secured to said conduit, said openings being configured in size for receiving the lamp tubing of said radiation lamp therethrough into the interior of said conduit and for enabling the flange to interface with the mounting member to restrict axial movement of the lamp base into the interior of said conduit;
   a coupling member for detachably securing the lamp base to said mounting member;
   an electrical socket for receiving the electrical terminal pins of said lamp base, said socket being detachably mounted to said coupling member in a manner that prevents detachment of the coupling member from said mounting member without prior detachment of the socket from the electrical terminal pins of said lamp base; and optionally,
   electric transmission means connected to said socket and at least one ballast for powering said radiation lamp.

2. The air disinfection assembly according to claim 1 wherein said mounting member is detachably secured to said conduit with a fastening means.

3. The air disinfection assembly according to claim 1 wherein said coupling member comprises a fastening means that detachably secures said collar member to said mounting member.

4. The air disinfection assembly according to claim 1 wherein the mounting member is of a plate-like construction.

5. The air disinfection assembly according to claim 3 wherein the coupling member comprises an annular collar whose annular opening is configured for receiving therein the lamp base that supports said terminal pins.

6. The air disinfection assembly according to claim 5 wherein the electrical socket includes an obstruction member that obstructs access to the fastening means that detachably secures the annular collar to said mounting member.

7. The air disinfection assembly according to claim 5 wherein an annular obstruction member is disposed between said socket and said annular collar for preventing access to the fastening means of said annular collar.

8. A radiation module comprising
   a radiation lamp including a lamp base that supports a lamp tubing at one end thereof, said lamp base including a retention member and a plurality of axially extending terminal pins;
   a mounting member provided with an opening that receives the lamp tubing of said radiation lamp therethrough, said opening being configured in size to enable the retention member of said lamp base to restrict the axial movement of the lamp base beyond said mounting member;
   a coupling member mounted to said mounting member for detachably securing the lamp base to said mounting member;
   an electrical coupling member for receiving the electrical terminal pins of said lamp base, said electrical coupling member being configured to detachably mount to said coupling member in a manner that prevents detachment of the collar member from said mounting member without prior decoupling of the electrical coupling member from the electrical terminal pins of said lamp base; and optionally,
   electric transmission means connected to said electrical coupling member and at least one ballast for powering said radiation lamp.

9. The radiation module according to claim 8 wherein said retention member is a flange.

10. The radiation module according to claim 8 wherein said coupling member comprises an annular collar member whose annular opening is configured for receiving therein the lamp base which supports said terminal pins, said collar member including fastening means for its detachable securement to said mounting member.

11. The radiation module according to claim 8 wherein the electrical coupling member comprises an electrical socket that includes receptacles for receiving said terminal pins.

12. The radiation module according to claim 11 wherein said electrical socket includes an obstruction member that obstructs access to the fastening means of said collar member.

13. The radiation module according to claim 11 wherein an annular obstruction member is disposed between said electrical socket and said collar member for preventing access to the fastening means of said collar member.

14. The radiation module according to claim 13 wherein the interior annulus of said collar member is threaded, and the electrical socket comprises an exteriorly threaded cylindrical member that includes axially extending electrical receptacles therein, said cylindrical member axially extending through said annular obstruction member for threaded engagement with the interior annulus of said collar member to connect the terminal pins of said lamp base with said electrical receptacles.

15. A radiation module for incorporation with a conduit containing the passage of air therethrough, comprising
    (a) a radiation lamp including a lamp base that supports a lamp tubing at one end thereof, said lamp base comprising:
        (i) a mounting member disposed about the end thereof and sized for detachable securement to said conduit; and
        (ii) a plurality of terminal pins axially extending from said mounting member;
    (b) an electrical coupling member detachably mounted to said mounting member for electrical engagement with the terminal pins of said lamp base in a manner that prevents detachment of the mounting member from said conduit without prior detachment of the electrical coupling member from the terminal pins of said lamp base; and optionally
    (d) electric transmission means connected to said socket for powering said radiation lamp.

16. The radiation module according to claim 15 wherein the mounting member is integral with the lamp base.

17. The radiation module according to claim 15 wherein the electrical coupling member comprises an electrical socket that includes electrical receptacles for receiving the terminal pins of said lamp base.

18. The radiation module according to claim 17 wherein the mounting member is detachably secured to the conduit with a fastening means.

19. The radiation module according to claim 18 wherein the electrical socket obstructs access to said fastening means when the electrical socket is mounted to said mounting member.

20. The radiation module according to claim 19 wherein the fastening means comprises threaded fasteners.

21. The radiation module according to claim 15 additionally comprising a radiation pervious protective sleeve encompassing said radiation lamp wherein the protective sleeve is closed at one end and open at the opposite end for slidable mounting about radiation lamp, the open end of said protective sleeve interfacing with and secured to said mounting member.

22. A radiation module comprising
    a radiation lamp including a lamp base that supports two or more lamp tubings at one end thereof, said lamp base including a plurality of axially extending terminal pins;
    a mounting member provided with an opening for receiving the lamp tubings therethrough;
    a retention member for restricting the axial passage of said lamp base through the opening of said mounting member;
    a locking member disposed about said opening for detachably securing said lamp base to said mounting member;
    an electrical coupling member for electrical engagement of said terminal pins, said electrical coupling member being detachably secured to said mounting member in a manner that prevents detachment therefrom without prior disengagement of the electrical coupling member from the terminal pins of said lamp base; and optionally
    electric transmission means connected to said electrical coupling member and at least one ballast for powering said radiation lamp.

23. The radiation module according to claim 22 wherein said retention member is a flange means disposed about the opening in said mounting member.

24. The radiation module according to claim 23 wherein said locking member comprises one or more resilient clasps for detachable engagement with said lamp base.

25. The radiation module according to claim 24 wherein the electrical coupling member comprises an electrical socket that includes electrical receptacles for receiving said terminal pins.

26. The radiation module according to claim 25 wherein said electrical socket comprises an obstruction member that detachably mounts to said mounting member about said locking member thereby preventing access to said locking member.

27. The radiation module according to claim 26 wherein said obstruction member includes an extension disposed about at least a portion of the perimeter of said electrical socket, said extension being provided with fastening means that detachably secures the electrical socket to said mounting member.

28. The radiation module according to claim 27 wherein said extension comprises a lip disposed about the perimeter of said electrical socket, said lip being configured to interface with said mounting member about said locking member, and provided with at least one opening to accommodate the insertion of the fastening means for the detachable securement of the electrical socket to said mounting member.

29. The radiation module defined by claims 1, 8, 15 or 22 wherein said lamp base supports four, axially extending, electrical terminal pins.

30. The radiation module defined by claims 1, 8, 15 or 22 wherein said lamp base supports two, axially extending, electrical terminal pins.

31. The radiation module defined by claims 1, 8, 15, 22 or 35 additionally comprising a radiation pervious protective sleeve encompassing said radiation lamp.

32. The radiation module according to claim 31 wherein the protective sleeve is closed at one end, and open at the opposite end for slidable mounting to said radiation lamp.

33. The radiation module according to claim 32 wherein the open end of said protective sleeve is secured about one end of said radiation lamp.

34. The radiation module according to claim 33 wherein said protective sleeve is constructed of fused quartz.

35. A radiation module comprising
    a radiation lamp for generating ultraviolet light including a retaining means for supporting one or more one-sided tubings at one end thereof and a plurality of axially extending electrical conductor means;
    means defining a retention member disposed about said retaining means;
    mounting means provided with an opening for receiving said tubing therethrough, said opening being configured in size to enable the retention member to restrict axial movement of said retaining means beyond said mounting means;
    coupling means for detachably securing the retaining means to said mounting means including fastening means for detachably securing said coupling means to said mounting means;
    electrical receptacle means for detachably receiving said electrical conductor means;
    means for detachably mounting said electrical receptacle means to said coupling means in a manner that prevents detachment of said coupling means from said mounting means without prior detachment of the electrical receptacle means from said electrical conductor means; and optionally, electric transmission means connected to said electrical receptacle means for powering the radiation lamp.

36. The radiation module according to claim 35 wherein the electrical receptacle means obstructs access to said fastening means of said coupling means when mounted to said coupling means.

* * * * *